(12) United States Patent
Hong et al.

(10) Patent No.: US 12,404,226 B2
(45) Date of Patent: Sep. 2, 2025

(54) METHOD FOR ADDITION REACTION OF ACETYLENE AND KETONE COMPOUND

(71) Applicant: ASYMCHEM LIFE SCIENCE (TIANJIN) CO., LTD., Tianjin (CN)

(72) Inventors: Hao Hong, Morrisville, NC (US); Jiangping Lu, Tianjin (CN); Xichun Feng, Tianjin (CN); Xin Zhang, Tianjin (CN); Bo Yan, Tianjin (CN)

(73) Assignee: ASYMCHEM LIFE SCIENCE (TIANJIN) CO., LTD., Tianjin (CN)

( * ) Notice: Subject to any disclaimer, the term of this patent is extended or adjusted under 35 U.S.C. 154(b) by 673 days.

(21) Appl. No.: 17/642,937

(22) PCT Filed: Sep. 17, 2019

(86) PCT No.: PCT/CN2019/106220
§ 371 (c)(1),
(2) Date: Mar. 14, 2022

(87) PCT Pub. No.: WO2021/051275
PCT Pub. Date: Mar. 25, 2021

(65) Prior Publication Data
US 2022/0380280 A1    Dec. 1, 2022

(51) Int. Cl.
*C07C 29/42* (2006.01)
*B01J 10/00* (2006.01)
(Continued)

(52) U.S. Cl.
CPC ............. *C07C 29/42* (2013.01); *B01J 10/002* (2013.01); *B01J 19/0013* (2013.01);
(Continued)

(58) Field of Classification Search
CPC ......... C07C 29/42; C07C 41/48; C07C 41/26; B01J 10/002; B01J 19/0013; B01J 19/242; B01J 2219/00033; B01J 2219/00094
See application file for complete search history.

(56) References Cited

U.S. PATENT DOCUMENTS 3,954,669 A * 5/1976 Broecker ............... B01J 23/745
                                                              502/154
6,828,468 B2   12/2004 Basf
6,956,141 B1 * 10/2005 Maas-Brunner ...... C07C 29/172
                                                              568/861

FOREIGN PATENT DOCUMENTS

CA        2340697 A1    2/2000
CN        1312784 A     9/2001
(Continued)

OTHER PUBLICATIONS

Brel ("Novel nucleotide phosphonate analogues with 1,2-oxaphophol-3-ene ring skeleton", Nucleic Acids Symposium Series No. 52, Oxford University Press, Sep. 2008, pp. 589-590). (Year: 2008).*
(Continued)

*Primary Examiner* — Medhanit W Bahta
(74) *Attorney, Agent, or Firm* — Dennemeyer & Associates LLC

(57) ABSTRACT

The disclosure discloses a method for an addition reaction of acetylene and a ketone compound. The method includes the following steps: S1, providing a continuous reaction device, wherein the continuous reaction device includes a plurality of bubble tubular reactors being connected with each other through connecting tubes; feeding a raw material solution containing the ketone compound and alkali into the plurality of bubble tubular reactors, and S3, under normal pressure, pumping acetylene from the bottom of the first bubble tubular reactor for the addition reaction. By applying the
(Continued)

technical solution of the invention, acetylene reacts with the ketone compound in the plurality of bubble tubular reactors arranged in series, which can ensure the sufficient gas-liquid contact time, and thus making full use of the acetylene gas, improving the utilization rate thereof, effectively reduing the amount of acetylene, reducing costs, and further improving the safety.

10 Claims, 1 Drawing Sheet

(51) Int. Cl.
 *B01J 19/00* (2006.01)
 *B01J 19/24* (2006.01)
 *C07C 29/38* (2006.01)
 *C07C 41/48* (2006.01)
(52) U.S. Cl.
 CPC ............ *B01J 19/242* (2013.01); *C07C 29/38* (2013.01); *C07C 41/48* (2013.01); *B01J 2219/00033* (2013.01); *B01J 2219/00094* (2013.01)

(56) References Cited

FOREIGN PATENT DOCUMENTS

| CN | 102076701 A | 5/2011 |
| CN | 105924330 A | 9/2016 |
| CN | 109796304 A | 5/2019 |
| CN | 109897010 A | 6/2019 |
| CN | 110540489 A | 12/2019 |
| JP | 55129234 A | 10/1980 |
| JP | 56156226 A | 12/1981 |
| JP | 2001199913 A | 7/2001 |
| KR | 100880081 B1 | 1/2009 |
| WO | 2010119448 A1 | 10/2010 |

OTHER PUBLICATIONS

JPS6379852 (A), Apr. 9, 1988, English Abstract only (Year: 1988).*
International Search Report issued in connection with PCT Application No. PCT/CN2019/106220 dated Jun. 19, 2020.

* cited by examiner

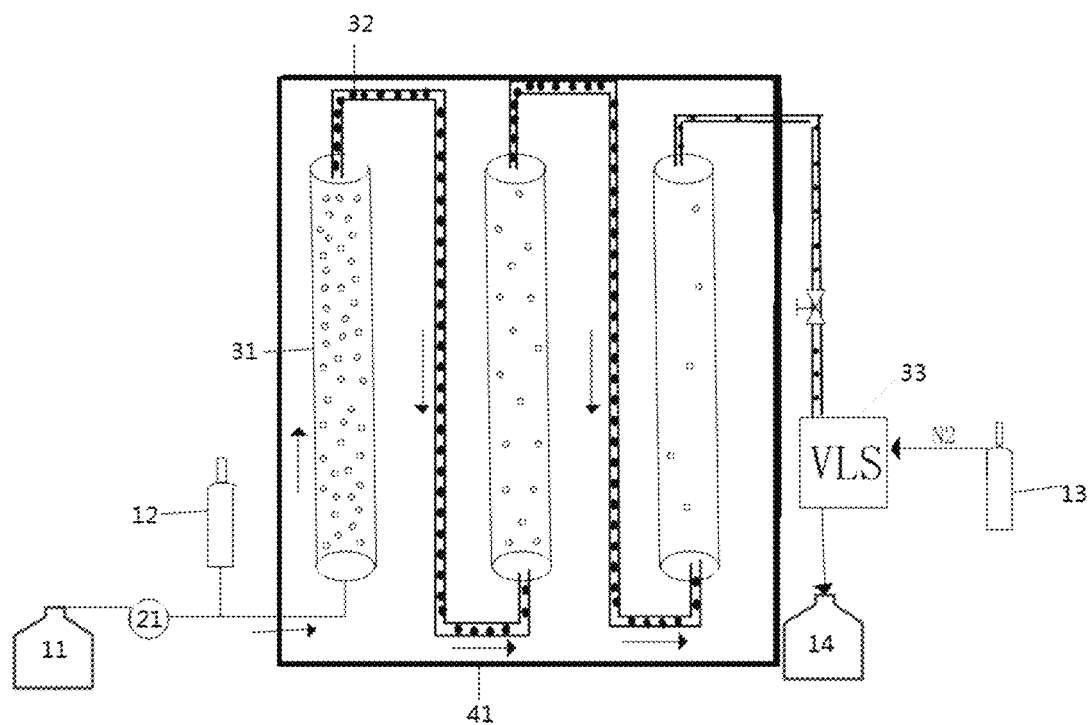

METHOD FOR ADDITION REACTION OF ACETYLENE AND KETONE COMPOUND

CROSS-REFERENCE TO RELATED APPLICATIONS

This is a 35 U.S.C. 371 National Stage Patent Application of International Application No. PCT/CN2019/106220, filed Sep. 17, 2019, which is hereby incorporated by reference in its entirety.

TECHNICAL FIELD

The disclosure relates to the technical field of organic synthesis, in particular to a method for an addition reaction of acetylene and a ketone compound.

BACKGROUND

Acetylene is a colorless and aromatic flammable gas with a flash point of −17.78° C. and a spontaneous combustion point of 305° C. The explosion limit in air is 2.3% to 72.3%. In the liquid and solid state, or in the gaseous state and under certain pressure, acetylene has a risk of violent explosion, and an explosion can be triggered when acetylene is subject to heat, vibration, electric sparks and other factors.

The addition reaction between acetylene and the ketone compound is very important in the field of organic synthesis. For example, a key step in the synthesis of a potential anti-HIV reagent, 3', 4'-Di-O-(−)-camphanoyl-(+)-cis-khellactone (DCK, deoxycytidine kinase), is the addition reaction of acetylene gas and ketones under the action of a strong base. Acetylene, however, is an extremely flammable gas and has the risk of violent explosion under certain pressure. It is difficult for acetylene to be used directly in industrial production due to the great safety risks. For example, in Bioorganic and Medicinal Chemistry Letters 2004 vol. 14 #23p.5855-5857, it is documented that during laboratory studies, the demanded compounds are produced by direct addition reaction of acetylene gas and ketones by using potassium tert-butoxide as a strong base. However, this method is only limited to laboratory preparative application and cannot be popularized industrially on a large scale.

Therefore, in the field of organic synthesis, it is common to first enable acetylene gas to react with the strong base, for example, an acetylene-based Grignard reagent is prepared through reaction of acetylene and a Grignard reagent, and then the addition reaction of ketones and the acetylene-based Grignard reagent is completed. The above process method is described in the following document: Organic Letters 2013vol. 15 #2p. 238-241. However, acetylene gas is still needed in the process method, and therefore a great safety risk still exists in the large-scale production process. If the acetylene-based Grignard reagent is directly procured for use, the process cost is bound to multiply due to the high cost of the acetylene-based Grignard reagent.

In addition, according to a traditional batch reaction process, when industrial production is carried out, a reaction kettle usually has a huge reaction volume of more than several thousand liters. The structural design of the traditional batch reaction kettle is not suitable for gas-liquid two-phase reaction under the normal pressure, and acetylene gas needs to be fed into a reaction system all the time during the reaction. The acetylene gas is greatly excessive and has a low utilization rate, and it is likely for acetylene to accumulate in a reaction pipeline of the reaction kettle, as a result, a great safety hazard is caused.

SUMMARY

The disclosure aims to provide a method for addition reaction of acetylene and a ketone compound, so that the addition reaction of acetylene and the ketone compound can be carried out safely.

In order to achieve the above purpose, according to one aspect of the disclosure, a method for carrying out an addition reaction of acetylene and the ketone compound is provided. The method includes the following steps: S1, providing a continuous reaction device, wherein the continuous reaction device includes a plurality of bubble tubular reactors arranged in series, the plurality of bubble tubular reactors being connected with each other through connecting tubes; S2, feeding a raw material solution containing the ketone compound and alkali into the plurality of bubble tubular reactors; and S3, under normal pressure, pumping acetylene from the bottom of the first bubble tubular reactor for the addition reaction.

Further, in S2, the raw material solution is placed in a raw material tank, and the raw material solution is pumped into the plurality of bubble tubular reactors by a raw material pump.

Further, a temperature control jacket is provided on the periphery of the plurality of bubble tubular reactors.

Further, the method further includes the step of S4: feeding the reaction product discharged from the bubble tubular reactor into a gas-liquid separator for gas-liquid separation.

Further, acetylene separated in the gas-liquid separator is diluted with nitrogen gas and then discharged.

Further, he ketone compound is an alkyl ketone compound or a ketone compound with halogen or an alkoxy functional group; and preferably, the alkali is potassium/sodium tert-butoxide or potassium/sodium tert-pentoxide.

Further, when the ketone compound is

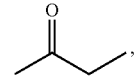

a reaction temperature of the bubble tubular reactors is controlled to be 0 to 5° C., the reaction time is controlled to be 0.5 to 4 h, and the molar ratio of

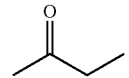

to acetylene is controlled to be (1.0-0.2):1.

Further, when the ketone compound is

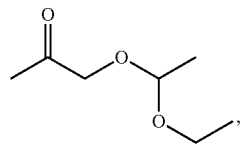

the reaction temperature of the bubble tubular reactors is controlled to be 10 to 15° C., the reaction time is controlled to be 0.5 to 4 h, and the molar ratio of

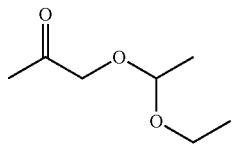

to acetylene is controlled to be (1.0-0.2):1.

Further, when the ketone compound is

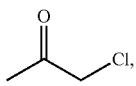

the reaction temperature of the bubble tubular reactors is controlled to be minus 40 to 30° C., the reaction time is controlled to be 0.5 to 4 h, and the molar ratio of

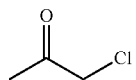

to acetylene is controlled to be (1.0-0.2):1.

By applying the technical solution of the disclosure, acetylene reacts with the ketone compound in the plurality of bubble tubular reactors arranged in series, which can ensure the sufficient gas-liquid contact time, and thus making full use of the acetylene gas, improving the utilization rate thereof, effectively reducing the amount of acetylene, reducing costs, and further improving the safety.

BRIEF DESCRIPTION OF THE DRAWINGS

The disclosure will be further explained by the accompanying drawings constituting one part of the disclosure. The illustrative embodiments of the disclosure and descriptions are used to explain the disclosure and do not constitute an improper limitation to the disclosure. In the accompanying drawings:

The figure illustrates a schematic structural drawing of a continuous reaction device of one embodiment of the disclosure.

DETAILED DESCRIPTION OF THE EMBODIMENTS

It is noted that the embodiments and features of the embodiments in the present disclosure can be combined with each other without conflict. The disclosure will be described in detail below with reference to the accompanying drawings and in conjunction with the embodiments.

In response to a series of technical problems described in the background technology, the present disclosure provides a gas-liquid two-phase continuous reaction process which can achieve efficient utilization of acetylene gas under normal pressure and can avoid the danger of accumulation of a large amount of acetylene gas during the reaction process, so that the process safety can be greatly improved, thus making the process more suitable for industrial production.

According to a typical embodiment of the disclosure, a method for the addition reaction of acetylene and the ketone compound is provided. The method includes the following steps: S1, providing a continuous reaction device, wherein the continuous reaction device includes a plurality of bubble tubular reactors arranged in series, the plurality of bubble tubular reactors being connected with each other through connecting tubes; S2, feeding a raw material solution containing the ketone compound and alkali into the plurality of bubble tubular reactors; and S3, under normal pressure, pumping acetylene from the bottom of the first bubble tubular reactor for the addition reaction.

By applying the technical solution of the disclosure, acetylene reacts with the ketone compound in the plurality of bubble tubular reactors arranged in series, which can ensure the sufficient gas-liquid contact time, and thus making full use of the acetylene gas, improving the utilization rate thereof, effectively reducing the amount of acetylene, reducing costs, and further improving the safety. In addition, the disclosure adopts a continuous reaction device, the production of thousands of liters of reaction system can be completed through a smaller reactor volume, for example, the volume of the reactor of the production level of the continuous reaction device can be only 100 L, and can be reduced to be smaller according to the production requirements, so that accumulation of acetylene gas and solution after dissolution of acetylene gas can be effectively avoided, and danger can be controlled more easily.

The number of bubble tubular reactors can be increased or decreased according to the process needs, with the aim of ensuring sufficient gas-liquid contact time to maximize the acetylene utilization rate. Preferably, in S2, the raw material solution is placed in a raw material tank, and the raw material solution is pumped into the plurality of bubble tubular reactors by a raw material pump to facilitate industrial production.

In order to facilitate the temperature control, a temperature control jacket is arranged on the periphery of the plurality of bubble tubular reactors.

Preferably, the method further includes the step of S4: tfeeding the reaction product discharged from the bubble tubular reactor into a gas-liquid separator for gas-liquid separation, and the small amount of acetylene tail gas produced during the process operation can be evacuated in the gas-liquid separator after sufficient dilution by nitrogen gas to maximize the process safety.

The technical solution of the disclosure can be applied to the ketone compound that is compatible with strong alkaline reagents, such as potassium tert-butoxide, and potassium acetylide, wherein ketone compound includes an alkyl ketone compound, and the ketone compound with a halogen or an alkoxy functional group, etc.

When the technical solution of the disclosure is applied, specific reaction conditions need to be determined according to the specific ketone compound. For example, when the ketone compound is

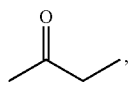

the reaction temperature of the bubble tubular reactors is controlled to be 0 to 5° C., the reaction time is controlled to be 0.5 to 4 h, preferably 2 h, and the molar ratio of

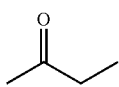

to acetylene is controlled to be (1.0-0.2):1; when the ketone compound is

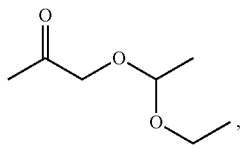

the reaction temperature of the bubble tubular reactors is controlled to be 10 to 15° C. and the reaction time is controlled to be 0.5 to 4 h, preferably 30 minutes, and the molar ratio of

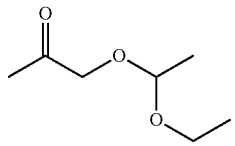

to acetylene is controlled to be (1.0-0.2):1; preferably, when the ketone compound is

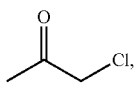

the reaction temperature of the bubble tubular reactors is controlled to be minus 40 to 30° C., the reaction time is controlled to be 0.5 to 4 h, preferably 3 h, and the molar ratio of

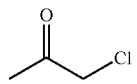

to acetylene is controlled to be (1.0-0.2):1.

In one embodiment of the disclosure, the continuous reaction device is shown in the figure and includes a power system and a continuous reactor, and further includes a raw material tank 11, an acetylene gas cylinder 12, a nitrogen gas cylinder 13, a receiving tank 14 and a temperature control jacket 41 for controlling the reactor temperature, wherein the power system includes a raw material pump 21, a first bubble tubular reactor 31, a second bubble tubular reactor and a third bubble tubular reactor jointly constitute a continuous gas-liquid two-phase reactor. In the whole set of reactors, the first bubble tubular reactor 31, the second bubble tube reactor and the third bubble tube reactor with larger diameters are connected in series via a connecting tube with a smaller diameter. The raw material tank 11 is used for storing the prepared main raw material/strong alkali solution. The raw material is pumped into the reactor by the raw material pump 21 after the technological process is started. The flow rate of acetylene in the acetylene gas cylinder 12 can be controlled by any gas flow rate controller, e.g. a gas mass flow meter. The acetylene gas released from the acetylene gas cylinder 12 is mixed with the raw material solution and enters from the lower end of the first bubble tubular reactor 31. The temperatures required by the first bubble tubular reactor 31, the second bubble tubular reactor and the third bubble tubular reactor are controlled by the temperature control jacket 41. In the first bubble tubular reactor 31, acetylene gas flows upward in a bubble shape. The raw material solution flows upward as a continuous phase. When reaching the upper end of a tubular reactor, the reaction system reaches the bottom of the next second bubble tubular reactor through a thinner connecting tube 32 between the first bubble tubular reactor 31 and the second bubble tubular reactor. The reaction system continuously flows to the outlet ends of the reactors in a reciprocating manner. The acetylene gas is in a bubble shape in the first bubble tubular reactor 31 and the flow rate of acetylene gas is greater than that of liquid. In the second bubble tubular reactor, the acetylene gas and liquid flow in a sectional type, and the flow rate of acetylene gas is the same as that of liquid. For the whole set of reactors, the number of the bubble tubular reactors can be adjusted according to the required reaction time (gas-liquid contact time). Since the set of reactors can ensure sufficient gas-liquid contact time, the acetylene gas can be fully utilized instead of excessive acetylene gas needed in the conventional batch reaction process. As shown in the figure, there are a large quantity of acetylene gas in the first bubble tubular reactor 31. As the acetylene gas and liquid flow backward, the number of bubbles in the second bubble tubular reactor and the third bubble tubular reactor gradually decreases. The outlet of the third bubble tubular reactor is connected to a gas-liquid separator 33. Excessive acetylene gas can be diluted here by nitrogen to compliance and then evacuated. Finally, the reacted system is received by the receiving tank 14.

The beneficial effects of the disclosure will be further illustrated below in combination with the embodiments.

Embodiment 1

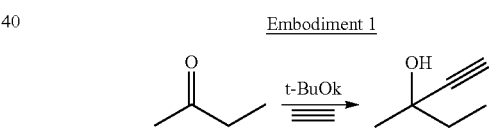

According to the above reaction formula, the reaction is carried out by adopting the device (continuous reaction device) and a batch reaction process shown in the figure, and the specific parameters and results are shown in Table 1.

The raw materials namely ketones and potassium tert-butoxide are dissolved in tetrahydrofuran, and the formed solution is named as SM solution, wherein the volume of tetrahydrofuran is ten times of that of ketones. The SM solution is connected with a feed pump in the reaction device. The temperature of the reaction device is adjusted to a specified temperature. The feed rate of the SM solution is calculated according to the size of the reactor and the required reaction time. The feed rate of acetylene is calculated according to the feed rate of the SM solution and the required equivalent weight acetylene. An SM solution feed pump and the acetylene cylinder are started at the same time, and the reaction device is fed at the same time according to the set flow rate. Samples are taken at a sampling point at the outlet of the reaction device, and the reaction condition is tracked and monitored. After all the SM solution is pumped into the reaction device, the solvent tetrahydrofuran is continuously pumped into the reaction device to displace the whole reaction system to a receiving bottle or a receiving kettle.

TABLE 1

| Process type | Production scale | Reactor | Temperature | t-BuOK | Acetylene | Reaction time or residence time | Yield | Acetylene utilization rate |
|---|---|---|---|---|---|---|---|---|
| Batch reaction process | 10 g | 500 mL of glass bottle | 0-5° C. | 1.0 eq. | 10 eq. | 2 h | 95% | 10% |
| Continuous reaction process | 10 g | Continuous gas-liquid two-phase reactor, and liquid holdup: 35 mL | 0-5° C. | 1.0 eq. | 1.2 eq. | 2 h | 96% | 83.3% |
| | 10 g | Continuous gas-liquid two-phase reactor, and liquid holdup: 35 mL | 0-5° C. | 1.0 eq. | 1.0 eq. | 2 h | 91% | 95% |
| | 10 g | Continuous gas-liquid two-phase reactor, and liquid holdup: 35 mL | 0-5° C. | 1.0 eq. | 5.0 eq. | 2 h | 96% | 20% |
| | 10 g | Continuous gas-liquid two-phase reactor, and liquid holdup: 35 mL | 0-5° C. | 1.0 eq. | 1.2 eq. | 0.5 h | 88% | 76% |
| | 10 g | Continuous gas-liquid two-phase reactor, and liquid holdup: 35 mL | 0-5° C. | 1.0 eq. | 1.2 eq. | 4 h | 95% | 83.3% |
| | 100 Kg | Continuous gas-liquid two-phase reactor, and liquid holdup: 50 L | 0-5° C. | 1.0 eq. | 1.2 eq. | 2 h | 95% | 83.3% |

Embodiment 2

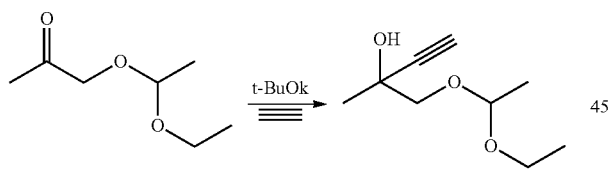

40

45

According to the above reaction formula, the reaction is carried out by adopting the device shown in the figure, for the steps, read the embodiment 1 for reference, and the specific parameters and results are shown in Table 2.

TABLE 2

| Process type | Production scale | Reactor | Temperature | t-BuOK | Acetylene | Reaction time or residence time | Yield | Acetylene utilization rate |
|---|---|---|---|---|---|---|---|---|
| Batch reaction process | 10 g | 500 mL of glass bottle | 10-15° C. | 1.0 eq. | 20 eq. | 1 h | 83% | 5% |
| Continuous reaction process | 10 g | Continuous gas-liquid two-phase reactor, and liquid holdup: 35 mL | 10-15° C. | 1.0 eq. | 1.5 eq. | 30 min | 91% | 66.7% |

TABLE 2-continued

| Process type | Production scale | Reactor | Temperature | t-BuOK | Acetylene | Reaction time or residence time | Yield | Acetylene utilization rate |
|---|---|---|---|---|---|---|---|---|
| | 10 g | Continuous gas-liquid two-phase reactor, and liquid holdup: 35 mL | 10-15° C. | 1.0 eq. | 1.0 eq. | 30 min | 87% | 64% |
| | 10 g | Continuous gas-liquid two-phase reactor, and liquid holdup: 35 mL | 10-15° C. | 1.0 eq. | 5.0 eq. | 30 min | 91% | 20% |
| | 10 g | Continuous gas-liquid two-phase reactor, and liquid holdup: 35 mL | 10-15° C. | 1.0 eq. | 1.5 eq. | 2 h | 90% | 66.7% |
| | 10 g | Continuous gas-liquid two-phase reactor, and liquid holdup: 35 mL | 10-15° C. | 1.0 eq. | 1.5 eq. | 4 h | 90% | 66.7% |
| | 100 Kg | Continuous gas-liquid two-phase reactor, and liquid holdup: 50 L | 10-15° C. | 1.0 eq. | 1.5 eq. | 30 min | 93% | 66.7% |

Embodiment 3

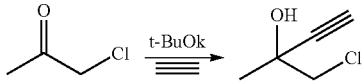

According to the above reaction formula, the reaction is carried out by adopting the device shown in the figure, for the steps, read the embodiment 1 for reference, and the specific parameters and results are shown in Table 3.

TABLE 3

| Process type | Production scale | Reactor | Temperature | t-BuOK | Acetylene | Reaction time or residence time | Yield | Acetylene utilization rate |
|---|---|---|---|---|---|---|---|---|
| Batch reaction process | 10 g | 500 mL of glass bottle | −40 to 30° C. | 10 .eq. | 8 eq. | 5 h | 75% | 12.5% |
| Continuous reaction process | 10 g | Continuous gas-liquid two-phase reactor, and liquid holdup: 35 mL | −40 to 30° C. | 10 .eq. | 1.1 eq. | 3 h | 86% | 90.9% |
| | 10 g | Continuous gas-liquid two-phase reactor, and liquid holdup: 35 mL | −40 to 30° C. | 10 .eq. | 1.0 eq. | 3 h | 84% | 88.8% |

TABLE 3-continued

| Process type | Production scale | Reactor | Temperature | t-BuOK | Acetylene | Reaction time or residence time | Yield | Acetylene utilization rate |
|---|---|---|---|---|---|---|---|---|
| | 10 g | Continuous gas-liquid two-phase reactor, and liquid holdup: 35 mL | −40 to 30° C. | 10 .eq. | 5.0 eq. | 3 h | 86% | 90.9% |
| | 10 g | Continuous gas-liquid two-phase reactor, and liquid holdup: 35 mL | −40 to 30° C. | 10 .eq. | 1.1 eq. | 0.5 h | 80% | 84.6% |
| | 10 g | Continuous gas-liquid two-phase reactor, and liquid holdup: 35 mL | −40 to 30° C. | 10 .eq. | 1.1 eq. | 4 h | 86% | 90.9% |
| | 100 Kg | Continuous gas-liquid two-phase reactor, and liquid holdup: 50 L | −40 to 30° C. | 10 .eq. | 1.1 eq. | 3 h | 85% | 90.9% |

The above embodiments indicate that the reaction can be successfully applied to large-scale production above 100 Kg level, the amplification effect is avoided, and the process is safe and reliable. The direct application of acetylene gas in the production level synthesis is successfully achieved. In addition, the acetylene utilization rate is greatly improved compared to the batch process, and further, the cost is saved and the process safety is improved.

From the above descriptions, it can be seen that the above embodiments of the disclosure achieve the following technical effects:

1) the small size of the reactor can effectively avoid the accumulation of large amounts of acetylene to minimize the danger in the reaction process;
2) the utilization rate of acetylene can be improved, the amount of acetylene can be effectively reduced, and the safety is further improved while saving the cost;
3) the slightly excessive acetylene gas does not accumulate, but is continuously diluted by diluted nitrogen gas and then evacuated at the gas-liquid separator during the process operation.

The above descriptions are only preferred embodiments of the disclosure, and are not intended to limit the disclosure, and the disclosure can have various alterations and variations for those skilled in the art. Any alteration, equivalent replacement, improvement and soon made within the spirit and principle of the disclosure shall been compassed by the protection scope of the disclosure.

The invention claimed is:

1. A method for addition reaction of acetylene and a ketone compound, comprising the steps of:
   S1, providing a continuous reaction device, the continuous reaction device comprising a plurality of bubble tubular reactors arranged in series, the plurality of bubble tubular reactors being connected with each other through connecting tubes;
   S2, feeding a raw material solution containing the ketone compound and alkali into the plurality of bubble tubular reactors, and
   S3, under normal pressure, pumping acetylene from the bottom of the first bubble tubular reactor for the addition reaction.

2. The method of claim 1, wherein in S2, the raw material solution is placed in a raw material tank, and the raw material solution is pumped into the plurality of bubble tubular reactors by a raw material pump.

3. The method of claim 1, wherein a temperature control jacket is provided on the periphery of the plurality of bubble tubular reactors.

4. The method of claim 1, wherein the method further comprises: S4, feeding the reaction product discharged from the bubble tubular reactor into a gas-liquid separator for gas-liquid separation.

5. The method of claim 4, wherein acetylene separated in the gas-liquid separator is diluted with nitrogen gas and then discharged.

6. The method of claim 1, wherein the ketone compound is an alkyl ketone compound or a ketone compound with halogen or an alkoxy functional group.

7. The method of claim 6, wherein controlling the reaction temperature of the bubble tubular reactors to 0 to 5° C. and the reaction time to 0.5 to 4 h when the ketone compound is

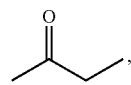
, wherein the molar ratio of

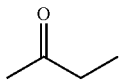

to acetylene is (1.0-0.2):1.

8. The method of claim 1, wherein controlling the reaction temperature of the bubble tubular reactors to 10 to 15° C. and the reaction time to 0.5 to 4 h when the ketone compound is

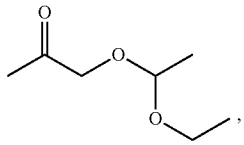

wherein the molar ratio of

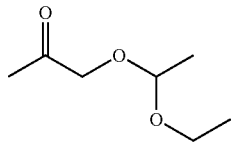

to acetylene is (1.0-0.2):1.

9. The method of claim 1, wherein controlling the reaction temperature of the bubble tubular reactors to −40 to 30° C. and the reaction time to 0.5 to 4 h when the ketone compound is

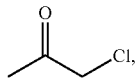

wherein the molar ratio of

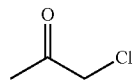

to acetylene is (1.0-0.2):1.

10. The method of claim 1, wherein the alkali is potassium/sodium tert-butoxide or potassium/sodium tert-pentoxide.

* * * * *